(12) United States Patent
Noll et al.

(10) Patent No.: US 10,881,883 B2
(45) Date of Patent: Jan. 5, 2021

(54) COSMETIC AGENT FOR TEMPORARILY RESHAPING KERATINOUS FIBERS WITH NATURAL PETROLEUM JELLY

(71) Applicant: Henkel AG & Co. KGaA, Duesseldorf (DE)

(72) Inventors: Marcus Noll, Quickborn (DE); Sandra Brandt, Pinneberg (DE); Nora Koopmann, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/676,126

(22) Filed: Nov. 6, 2019

(65) Prior Publication Data
US 2020/0155873 A1 May 21, 2020

(30) Foreign Application Priority Data
Nov. 15, 2018 (DE) .......................... 10 2018 219 507

(51) Int. Cl.
| | | |
|---|---|---|
| *A61Q 5/00* | (2006.01) | |
| *A61Q 5/10* | (2006.01) | |
| *A61K 8/22* | (2006.01) | |
| *A61K 8/81* | (2006.01) | |
| *A61Q 5/06* | (2006.01) | |
| *A61Q 5/08* | (2006.01) | |
| *A61Q 5/12* | (2006.01) | |

(52) U.S. Cl.
CPC ................ *A61Q 5/10* (2013.01); *A61K 8/22* (2013.01); *A61K 8/8152* (2013.01); *A61Q 5/06* (2013.01); *A61Q 5/08* (2013.01); *A61Q 5/12* (2013.01)

(58) Field of Classification Search
CPC ... A61Q 5/10; A61Q 5/08; A61Q 5/12; A61Q 5/04; A61Q 5/06; A61K 8/22; A61K 8/342; A61K 8/92; A61K 47/44
USPC ....................................... 424/70.2, 70.4, 70.6
See application file for complete search history.

(56) References Cited

U.S. PATENT DOCUMENTS

| | | | | |
|---|---|---|---|---|
| 5,846,549 A | * | 12/1998 | Beauquey | ................ A61K 8/26 424/401 |
| 2017/0172902 A1 | * | 6/2017 | Puls | ......................... A61K 8/31 |
| 2017/0172905 A1 | * | 6/2017 | Puls | ........................ A61K 8/925 |
| 2017/0172907 A1 | * | 6/2017 | Puls | ........................ A61K 8/922 |
| 2017/0172908 A1 | * | 6/2017 | Puls | ...................... A61K 8/4953 |

FOREIGN PATENT DOCUMENTS

| | | |
|---|---|---|
| JP | 2003026551 A | 1/2003 |
| JP | 2012180296 A | 9/2012 |
| JP | 2017203050 A | 11/2017 |

* cited by examiner

*Primary Examiner* — Eisa B Elhilo
(74) *Attorney, Agent, or Firm* — Lorenz & Kopf, LLP

(57) ABSTRACT

Cosmetic agents for temporarily shaping keratin fibers, in particular human hair, are provided. In one example, a cosmetic agent includes, in each case in relation to the total weight of the composition, a) from about 10 to about 45% by weight of at least one clay mineral,
b) from about 30 to about 60% by weight of at least three natural fat compounds, and
c) from about 2 to about 15% by weight of at least one emulsifier.

19 Claims, No Drawings

COSMETIC AGENT FOR TEMPORARILY RESHAPING KERATINOUS FIBERS WITH NATURAL PETROLEUM JELLY

CROSS-REFERENCE TO RELATED APPLICATION

This application claims priority to German Patent Application No. 10 2018 219 507.2, filed Nov. 15, 2018, which is incorporated herein by reference in its entirety.

TECHNICAL FIELD

The present disclosure relates to cosmetic agents for temporarily shaping keratinous fibers, comprising a clay mineral, fat compounds and an emulsifier, and use thereof. The present disclosure also relates to a method that employs a cosmetic agent.

BACKGROUND

Cosmetic agents which serve to permanently or temporarily shape the hair (styling agents) play a key role in the field of cosmetics. Numerous cosmetic agents are thus known in the prior art, for example hairsprays, hair waxes, hair gels, hair mousses, pomades, hair waxes, hair lotions, etc.

What are known as "styling clays" are a relatively new class of styling products. These products have a very thick to very creamy consistency. A common feature of all styling clays is that they contain a clay. The clay makes the hair feel "fatter" by providing the individual hair strands with body, thickness and structure. Styling clays are suitable in particular for hairstyles which require a lot of volume (for example "out-of-bed" look).

Besides the clay, styling clays usually contain petroleum jelly (INCI: Petrolatum). Petroleum jelly is an ointment-like mixture of solid and liquid hydrocarbons from petroleum with a melting range from about 38 to about 58° C. Petroleum jelly is used in the styling clays in particular to protect the hair against ambient humidity and to support the shapeability. Petroleum jelly, however, often leads to a greasy/oily sheen on the hair treated with it. Furthermore, there is also a trend to replace petroleum-based raw materials by renewable and/or natural raw materials.

The problem addressed by the present disclosure is that of providing a clay-containing cosmetic agent which is suitable for temporarily reshaping keratinous fibers, in which the use of petroleum-based raw materials is considerably reduced or in which the use of petroleum-based raw materials is omitted, wherein the styling properties remain at a high level. In particular, hair treated with the cosmetic agent as contemplated herein should be provided with a medium to high hold, without developing a greasy/oily sheen.

The problem addressed by the present disclosure is solved by a cosmetic agent for temporarily shaping keratin fibers, in particular human hair, comprising—in each case in relation to the total weight of the composition—
a) from about 10 to about 45% by weight of at least one clay mineral,
b) from about 30 to about 60% by weight of at least three natural fat compounds, and
c) from about 2 to about 15% by weight of at least one emulsifier.

BRIEF SUMMARY

Cosmetic agents are provided herein. In an exemplary embodiment, a cosmetic agent for temporarily shaping keratin fibers includes, based on a total weight of the cosmetic agent, a) from about 10 to about 45% by weight of at least one clay mineral, b) from about 30 to about 60% by weight of at least three natural fat compounds, and c) from about 2 to about 15% by weight of at least one emulsifier.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has surprisingly been found that a cosmetic agent which contains not only a clay mineral and an emulsifier, but at least three natural fat compounds in a total amount of from about 30 to about 60% by weight, after application to keratin fibers, is able to temporarily shape the treated fibers with long-lasting effect and a high degree of hold. The keratin fibers are provided with a matt and dry, but not greasy appearance. Due to the uses of natural fat compounds instead of petroleum jelly, the use of petroleum-based raw materials could be significantly reduced, without having to make compromises with regard to the degree of hold and/or the appearance.

The term "keratin fibers" or "keratinous fibers" within the scope of the present disclosure shall be understood to mean furs, wool, feathers and hair, in particular human hair.

The cosmetic agent contains as component a) at least one clay mineral.

The term "clay mineral" on the one hand refers to minerals that occur primarily in the form of the finest grains (grain size <about 2 μm), but on the other hand may also include the phyllosilicates, which in accordance with their layer-like crystal structure are formed from silicon and oxygen, and also hydrogen and usually magnesium and aluminum. The definitions are not congruent.

It is preferred that the clay mineral is selected from the group including the kaolin group, the smectite group, the illite mica group, the chlorite group and mixtures thereof.

It is extremely preferred that the clay mineral comprises a phyllosilicate selected from the group including kaolinite, halloysite, dickite, nacrite, dioctahedral vermiculite, dioctahedral illite, dioctahedral smectite, montmorillonite, beidellite, nontronite, volconscoite, nacrite, trioctahedral vermiculite, trioctahedral smectite, saponite, hectorite, sauconite and mixtures thereof.

In a very particularly preferred embodiment the at least one clay mineral comprises kaolinite and/or montmorillonite.

Clay minerals can be added to the agent in the form of aluminum oxides. There are various aluminum oxides which are exemplified by a different composition of clay minerals and optionally phyllosilicates. Aluminum oxides exist in white, pink, red-yellow, brown and green. The color of green aluminum oxide is attributed to copper compounds. In the case of pinkish, red and brown aluminum oxide, iron is the chromophoric element. White aluminum oxide, which is also referred to as kaolin, denotes a fine, iron-free, white clay, which contains kaolinite as main constituent. In addition, halloysite, dickite and nacrite also occur.

It is particularly preferred that the cosmetic agent contains the at least one clay mineral in the form of a white aluminum oxide (INCI: Kaolin). Accordingly, it is preferred that the at least one clay mineral is selected from the group including kaolinite, halloysite, dickite, nacrite and mixtures thereof. In an extremely particularly preferred embodiment the at least one clay mineral comprises kaolinite, dickite and nacrite.

It may also be preferred that the at least one clay mineral is added in the form of bentonite. Bentonite is an aluminum oxide. Bentonite is a mixture of various clay minerals and contains montmorillonite as the most important constituent (from about 60% to about 80%).

It is also particularly preferred that the at least one clay mineral contains bentonite.

The amount of clay mineral is from about 10 to about 45% by weight, preferably from about 15 to about 40% by weight, and particularly preferably from about 20 to about 35% by weight, in each case in relation to the total weight of the agent.

The cosmetic agent contains as component b) at least three natural fat compounds. The cosmetic agent contains the at least three natural fat compounds in a total amount of from about 30 to about 60% by weight, preferably from about 35 to about 55% by weight, and even more preferably from about 40 to about 50% by weight, in relation to the total weight of the cosmetic agent.

It is preferred that the natural fat compounds are selected from the group including natural oils, natural waxes, natural fats and mixtures thereof.

In a preferred embodiment the at least three natural fat compounds comprise at least one natural oil and at least two natural waxes.

In a more preferred embodiment the at least three natural fat compounds comprise at least one natural oil and at least three natural waxes.

In an extremely preferred embodiment the at least three natural fat compounds comprise at least two natural oils and at least three natural waxes.

Vegetable triglycerides and mixtures of vegetable triglycerides may be used as natural oils. Preferred natural vegetable oils are coconut oil, (sweet) almond oil, walnut oil, peach stone oil, apricot kernel oil, avocado oil, tea tree oil, soybean oil, sesame oil, sunflower oil, tsubaki oil, evening primrose oil, rice bran oil, palm kernel oil, mango kernel oil, lady's smock oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil and castor oil.

Furthermore, natural carboxylic acid esters, such as myristic acid isopropyl ester, may be used as natural oils. Myristic acid isopropyl ester (INCI: Isopropyl myristate) occurs naturally for example in butter, palm kernel oil and coconut oil.

Animal triglycerides and mixtures of animal triglycerides may also be used as natural oils. A suitable natural, animal oil is mink oil, for example.

Vegetable waxes, such as candelilla wax, carnauba wax, (partially) hydrogenated castor oil, esparto grass wax, Japan wax, cork wax, sugar cane wax, ouricury wax, montan wax, sunflower wax, cotton wax, rice bran wax, flax wax, slack wax, rose wax, jasmine wax, Cuban palm wax, guaruma wax, Shea Butter (INCI: *Butyrospermum Parkii* (Shea) Butter), fruit waxes and animal waxes, such as beeswax and other insect waxes, spermaceti, shellac wax, lanolin and rump fat, may be used as natural waxes. It may be advantageous to use hydrogenated or hardened wax.

Vegetable fats, such as cocoa butter, coconut butter, palm fat, palm kernel fat, Bacuri butter, baobab seed oil and/or baobab tree oil may be used as natural fats. Suitable animal fats include, for example, lard and/or beef tallow.

In a particularly preferred embodiment the at least three natural fat compounds comprise a combination of castor oil (INCI: *Ricinus Communis* (Castor) Seed Oil), hydrogenated castor oil (INCI: Hydrogenated Castor Oil), and carnauba wax (INCI: *Copernicia Cerifera* (Carnauba) Wax).

In a very particularly preferred embodiment the at least three natural fat compounds comprise a combination of castor oil (INCI: *Ricinus Communis* (Castor) Seed Oil), hydrogenated castor oil (INCI: Hydrogenated Castor Oil), carnauba wax (INCI: *Copernicia Cerifera* (Carnauba) Wax) and beeswax (INCI: Cera Alba).

In an extremely preferred embodiment the cosmetic agent comprises a combination of castor oil (INCI: *Ricinus Communis* (Castor) Seed Oil), hydrogenated castor oil (INCI: Hydrogenated Castor Oil), carnauba wax (INCI: *Copernicia Cerifera* (Carnauba) Wax), beeswax (INCI: Cera Alba) and myristic acid isopropyl ester (INCI: Isopropyl myristate).

The cosmetic agent contains as component c) at least one emulsifier. The at least one emulsifier improves the ease with which the cosmetic agent can be washed out.

Alkoxylated fatty alcohols may be used preferably as emulsifier. The preferred emulsifiers offer the advantage of being obtainable from natural, non-fully synthetic raw material sources.

Accordingly, preferred cosmetic agents at least one emulsifier comprises an alkoxylated fatty alcohol.

An "alkoxylated fatty alcohol" is any fatty alcohol having a carbon chain of C5 or more, which also comprises at least one alkoxy group. The fatty alcohol may be selected for example from $C_9$-$C_{11}$ fatty alcohols, $C_{12}$-$C_{13}$ fatty alcohols, $C_{12}$-$C_{15}$ fatty alcohols, $C_{12}$-$C_{16}$ fatty alcohols, $C_{14}$-$C_{15}$ fatty alcohols, arachidyl alcohol, behenyl alcohol, capryl alcohol, cetearyl alcohol, cetyl alcohol, coconut alcohol, decyl alcohol, (hydrogenated) tallow alcohol, laurel alcohol, myristyl alcohol, oleyl alcohol, palm alcohol, palm kernel alcohol, stearyl alcohol and tridecyl alcohol.

The alkoxyl group may include in particular ethoxy and/or propoxy and/or butoxy groups. The alkoxylated fatty alcohol is particularly preferably an ethoxylated fatty alcohol.

The at least one alkoxy group of the "alkoxylated fatty alcohol" may be derived for example from an alkoxylation reaction with alkylene oxide, in particular ethylene oxide and/or propylene oxide.

It is preferred that the alkoxylated fatty alcohol is selected from the group including Ceteareth-2. Ceteareth-3, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40. Ceteareth-50, Ceteareth-55, Ceteareth-60, Ceteareth-80, Ceteareth-100, Laureth-1 Laureth-2, Laureth-3 Laureth-4, Laureth-5, Laureth-6, Laureth-7, Laureth-8, Laureth-9, Laureth-10, Laureth-11, Laureth-12, Laureth-3, Laureth-14, Laureth-15, Laureth-16, Laureth-20, Laureth-23, Laureth-25 Laureth-30, Laureth-40, Deceth-3, Deceth-5, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Steareth-2, Steareth-4, Steareth-6, Steareth-7, Steareth-10, Steareth-11, Steareth-13, Steareth-14, Steareth-15, Steareth-20, Steareth-21, Steareth-25, Steareth-27, Steareth-30, Steareth-40, Steareth-50. Steareth-100 and mixtures thereof.

The name Ceteareth-2 for example stands for a $C_{16}$-$C_{18}$ fatty alcohol with, on average, 2 ethylene oxide units per molecule.

In a very particularly preferred embodiment of the cosmetic agent the at least one alkoxylated fatty alcohol comprises Oleth-5.

Phosphate esters, in particular liquid phosphate esters, may preferably also be used as emulsifier. The term "liquid phosphate ester" refers to any phosphate ester that is liquid at about 20° C. Particularly preferred phosphate esters are trilaureth-4 phosphate (for example obtainable as Hostaphat KL 340D or SILAPHOS® TE 340), C8-C10 phosphate (for example obtainable as Crodafos 81 OA), PPG-5-Ceteth-10 phosphate (for example obtainable as Crodafos C10/5A), cetoleth-5 phosphate (for example obtainable as Crodafos™ CO5A), deceth-4 phosphate (for example obtainable as Crodafos™ D4A), glycereth-26 phosphate (for example obtainable as Crodafo GEA), oleth-5 phosphate and dioleyl phosphate (for example obtainable as Crodafos HCE), potassium C12-13 alkyl phosphate (for example obtainable as Crodafos™ 1213K), TEA C12-13 alkyl phosphate (for example obtainable as Crodafos™ 1213T), C9-15 alkyl phosphate (for example obtainable as Crodafos M915A), oleth-10 phosphate (for example obtainable as Crodafos O10A), DEA oleth-10 phosphate (for example available as Crodafos™ O10D), oleth-3 phosphate (for example obtainable as Crodafos O3A), DEA oleth-3 phosphate (for example obtainable as Crodafos O3D), trideceth-10 phosphate (for example obtainable as Crodafos T10A), trideceth-5 phosphate (for example obtainable as Crodafos T5A) or trideceth-6 phosphate (for example obtainable as Crodafos™ T6A). Mixtures of phosphate esters may also be used. Trilaureth-4 phosphate is used most preferably.

In a very particularly preferred embodiment of the cosmetic agent the at least one emulsifier comprises trilaureth-4 phosphate.

In a very particularly preferred embodiment of the cosmetic agent the at least one emulsifier comprises an alkoxylated fatty alcohol and a phosphate ester.

In an extremely preferred embodiment the at least one emulsifier comprises an alkoxylated fatty alcohol and trilaureth-4 phosphate.

The amount of the at least one emulsifier is preferably from about 2 to about 15% by weight, and more preferably from about 4 to about 12% by weight, in each case in relation to the total amount of cosmetic agent.

The applicability of the cosmetic agent in the hair and the hair feel (hold) after application of the cosmetic agent can be further increased by the use of a fatty acid. Preferred cosmetic agents therefore also contain at least one C8 to C24 fatty acid, more preferably C12 to C22 fatty acid. The cosmetic agent particularly preferably contains palmitic acid and/or stearic acid. In relation to the total weight of the cosmetic agent, in a preferred embodiment of the present disclosure from about 1 to about 10% by weight, more preferably from about 4 to about 8% by weight, in each case in relation to the total weight of the cosmetic agent, of at least one C8 to C24 fatty acid are contained in the cosmetic agent.

In further preferred embodiments of the present disclosure the cosmetic agent also optionally contains further auxiliaries, such as preservatives, perfume and/or dyes.

The cosmetic agents are preferably provided in paste form. Pots in particular are a potential container for the cosmetic agent for temporarily reshaping keratin fibers.

Very particularly preferred cosmetic agents comprise at least one of the following embodiments A) to H):

A)
A cosmetic agent for temporarily shaping keratin fibers, in particular human hair, comprising—in each case in relation to the total weight of the composition—
a) from about 10 to about 45% by weight of at least one clay mineral, comprising kaolinite and/or montmorillonite,
b) from about 30 to about 60% by weight of at least three natural fat compounds, and
c) from about 4 to about 10% by weight of at least one emulsifier.

B)
A cosmetic agent for temporarily shaping keratin fibers, in particular human hair, comprising—in each case in relation to the total weight of the composition—
a) from about 10 to about 45% by weight of at least one clay mineral, comprising kaolinite and/or montmorillonite,
b) from about 30 to about 60% by weight of at least three natural fat compounds, and
c) from about 4 to about 10% by weight of at least one emulsifier, comprising an alkoxylated fatty alcohol and/or a phosphate ester.

C)
A cosmetic agent for temporarily shaping keratin fibers, in particular human hair, comprising—in each case in relation to the total weight of the composition—
a) from about 10 to about 45% by weight of at least one clay mineral, comprising kaolinite and/or montmorillonite,
b) from about 30 to about 60% by weight of at least three natural fat compounds, and
c) from about 4 to about 10% by weight of at least one emulsifier, comprising an alkoxylated fatty alcohol and a phosphate ester.

D)
A cosmetic agent for temporarily shaping keratin fibers, in particular human hair, comprising—in each case in relation to the total weight of the composition—
a) from about 10 to about 45% by weight of at least one clay mineral, comprising kaolinite and/or montmorillonite,
b) from about 30 to about 60% by weight of at least three natural fat compounds, comprising at least one natural oil and at least two natural waxes, and
c) from about 4 to about 10% by weight of at least one emulsifier, comprising an alkoxylated fatty alcohol and/or a phosphate ester.

E)
A cosmetic agent for temporarily shaping keratin fibers, in particular human hair, comprising—in each case in relation to the total weight of the composition—
a) from about 10 to about 45% by weight of at least one clay mineral, comprising kaolinite and/or montmorillonite,
b) from about 30 to about 60% by weight of at least three natural fat compounds, comprising at least one natural oil selected from the group including castor oil (INCI: *Ricinus Communis* (Castor) Seed Oil), myristic acid isopropyl ester (INCI: Isopropyl Myristate) an mixtures thereof and at least two natural waxes selected from the group including hydrogenated castor oil (INCI: Hydrogenated Castor Oil), carnauba wax (INCI: *Copernicia Cerifera* (Carnauba) Wax) and beeswax (INCI: Cera Alba), and
c) from about 4 to about 10% by weight of at least one emulsifier, comprising an alkoxylated fatty alcohol and/or a phosphate ester.

F)
A cosmetic agent for temporarily shaping keratin fibers, in particular human hair, comprising—in each case in relation to the total weight of the composition— a) from about 10 to about 45% by weight of at least one clay mineral, comprising kaolinite and/or montmorillonite,
b) from about 30 to about 60% by weight of at least three natural fat compounds, comprising at least one natural oil selected from the group including castor oil (INCI: *Ricinus Communis* (Castor) Seed Oil), myristic acid isopropyl ester (INCI: Isopropyl Myristate) an mixtures thereof and at least two natural waxes selected from the group including hydrogenated castor oil (INCI: Hydrogenated Castor Oil), carnauba wax (INCI: *Copernicia Cerifera* (Carnauba) Wax), beeswax (INCI: Cera Alba) and mixtures thereof, and
c) from about 4 to about 10% by weight of at least one emulsifier, comprising an alkoxylated fatty alcohol and trilaureth-4 phosphate as phosphate ester.
G)
A cosmetic agent for temporarily shaping keratin fibers, in particular human hair, comprising—in each case in relation to the total weight of the composition—
a) from about 10 to about 45% by weight of at least one clay mineral, comprising kaolinite,
b) from about 30 to about 60% by weight of at least three natural fat compounds, comprising castor oil (INCI: *Ricinus Communis* (Castor) Seed Oil), myristic acid isopropyl ester (INCI: Isopropyl Myristate), hydrogenated castor oil (INCI: Hydrogenated Castor Oil), carnauba wax (INCI: *Copernicia Cerifera* (Carnauba) Wax) and beeswax (INCI: Cera Alba), and
c) from about 4 to about 10% by weight of at least one emulsifier, comprising an alkoxylated fatty alcohol and trilaureth-4 phosphate as phosphate ester.
H)
A cosmetic agent for temporarily shaping keratin fibers, in particular human hair, comprising—in each case in relation to the total weight of the composition—
d) from about 10 to about 45% by weight of at least one clay mineral, comprising kaolinite, halloysite, dickite and nacrite,
e) from about 30 to about 60% by weight of at least three natural fat compounds, comprising castor oil (INCI: *Ricinus Communis* (Castor) Seed Oil), myristic acid isopropyl ester (INCI: Isopropyl Myristate), hydrogenated castor oil (INCI: Hydrogenated Castor Oil), carnauba wax (INCI: *Copernicia Cerifera* (Carnauba) Wax) and beeswax (INCI: Cera Alba), and
from about 4 to about 10% by weight of at least one emulsifier, comprising an alkoxylated fatty alcohol and trilaureth-4 phosphate as phosphate ester.

A second subject of the present disclosure is the use of the cosmetic agent forming the first subject of the present disclosure for temporarily reshaping and/or fixing the form of keratin fibers, in particular human hair.

A third subject of the present disclosure is a method for temporarily reshaping keratin fibers, in particular human hair, exemplified in that the cosmetic agent forming the first subject of the present disclosure is applied to the keratin fibers.

It has proven to be preferred if the keratin fibers are not rinsed out once the agent forming the first subject of the present disclosure has taken effect, and instead are left on the fibers.

Features relating to preferred embodiments of the first subject of the present disclosure which have been described above only in that regard also apply accordingly, of course, to the second and third subjects as features of preferred embodiments.

The following example is intended to explain the subject matter of the present disclosure without in any way limiting it.

Example

| Ingredient | % by weight (active substance) |
|---|---|
| Beeswax (INCI: Cera Alba (Beeswax)) | 8 |
| Castor oil (INCI: Ricinus Communis (Castor) Seed Oil), hydrogenated castor oil (INCI: Hydrogenated Castor Oil), carnauba wax (INCI: Copernicia Cerifera (Carnauba) Wax)* | 34 |
| Carnauba wax (INCI: Copernicia Cerifera (Carnauba) Wax) | 5 |
| Myristic acid isopropyl ester (INCI: Isopropyl Myristate) | 2 |
| Palmitic acid, stearic acid | 6 |
| Oleth-5 | 3 |
| Trilaureth-4 phosphate | 8 |
| CI 77891 (Titanium Dioxide) | 1 |
| white aluminum oxide (INCI: Kaolin) | to 100 |

*Natural Petroleum Jelly Type A (ex Ceratec)

The formulation as contemplated herein had a paste-like consistency with very good distribution properties in the hair. The styling clay as contemplated herein was applied by hand to test subjects in order to fix the form of the hairstyle. The reshaped hair was provided with a strong, but flexible hold of the hairstyle. The appearance of the hair was matt, dry and in particular not greasy or oily.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for temporarily shaping keratin fibers comprising, based on a total weight of the cosmetic agent,
   a) at least 20% by weight of at least one clay mineral,
   b) from about 30 to about 60% by weight of at least three natural fat compounds, and
   c) from about 2 to about 15% by weight of at least one emulsifier.

2. The cosmetic agent according to claim 1, wherein the at least one clay mineral is a white aluminum oxide (INCI: Kaolin).

3. The cosmetic agent according to claim 1, wherein the at least one clay mineral is selected from the group of kaolinite, halloysite, dickite, nacrite, or combinations thereof.

4. The cosmetic agent according to claim 1, wherein the at least three natural fat compounds comprise at least one natural oil and at least two natural waxes.

5. The cosmetic agent according to claim 1, wherein the at least three natural fat compounds comprises at least one natural oil selected from the group of castor oil (INCI: *Ricinus Communis* (Castor) Seed Oil), myristic acid isopropyl ester (INCI: Isopropyl Myristate), or combinations thereof and at least two natural waxes selected from the group of hydrogenated castor oil (INCI: Hydrogenated Castor Oil), carnauba wax (INCI: *Copernicia Cerifera* (Carnauba) Wax), beeswax (INCI: Cera Alba), or combinations thereof.

6. The cosmetic agent according to claim 1, wherein the at least one emulsifier is selected from the group of alkoxylated fatty alcohols, phosphate esters, or combinations thereof.

7. The cosmetic agent according to claim 1, wherein the cosmetic agent further comprises at least one fatty acid having from 8 to 24 carbon atoms.

8. A method for temporarily reshaping keratin fibers, wherein the cosmetic agent according to claim 1 is applied to the keratin fibers.

9. The cosmetic agent of claim 1, wherein the cosmetic agent comprises less than about 40% by weight of the at least one clay mineral.

10. The cosmetic agent of claim 9, wherein the cosmetic agent comprises less than about 45% by weight of the at least one clay mineral.

11. The cosmetic agent of claim 1, wherein the at least one clay mineral is selected from the group of kaolinite, montmorillonite, or combinations thereof.

12. The cosmetic agent of claim 1, wherein the cosmetic agent comprises from about 35 to about 55% by weight of the at least three natural fat compounds.

13. The cosmetic agent of claim 12, wherein the cosmetic agent comprises from about 40 to about 50% by weight of the at least three natural fat compounds.

14. The cosmetic agent of claim 1, wherein the at least one emulsifier comprises alkoxylated fatty alcohol.

15. The cosmetic agent of claim 14, wherein the alkoxylated fatty alcohol comprises Oleth-5.

16. The cosmetic agent of claim 1, wherein the cosmetic agent comprises from about 4 to about 12% by weight of the at least one emulsifier.

17. The cosmetic agent of claim 7, wherein the cosmetic agent comprises from about 1 to about 10% by weight of the at least one fatty acid.

18. The cosmetic agent of claim 17, wherein the cosmetic agent comprises from about 4 to about 8% by weight of the at least one fatty acid.

19. The cosmetic agent of claim 7, wherein the at least one fatty acid has from 12 to 22 carbon atoms.

* * * * *